(12) United States Patent
Palmer

(10) Patent No.: US 12,144,933 B2
(45) Date of Patent: Nov. 19, 2024

(54) METHODS OF MONITORING URINARY CATHETER USAGE

(71) Applicant: ConvaTec Inc., Bridgewater, NJ (US)

(72) Inventor: Timothy A. Palmer, Stillwater, MN (US)

(73) Assignee: CONVATEC INC., Bridgewater, IN (US)

( * ) Notice: Subject to any disclaimer, the term of this patent is extended or adjusted under 35 U.S.C. 154(b) by 871 days.

(21) Appl. No.: 17/202,756

(22) Filed: Mar. 16, 2021

(65) Prior Publication Data

US 2021/0196923 A1 Jul. 1, 2021

Related U.S. Application Data

(63) Continuation-in-part of application No. 17/097,941, filed on Nov. 13, 2020, now Pat. No. 10,946,168.

(60) Provisional application No. 62/936,994, filed on Nov. 18, 2019.

(51) Int. Cl.
*A61M 25/00* (2006.01)
*A61B 5/00* (2006.01)
*A61B 5/20* (2006.01)

(52) U.S. Cl.
CPC ......... *A61M 25/0017* (2013.01); *A61B 5/208* (2013.01); *A61B 5/6852* (2013.01);
(Continued)

(58) Field of Classification Search
CPC ...... A61M 25/0017; A61M 2205/3334; A61M 2210/1085; A61M 2210/1089;
(Continued)

(56) References Cited

U.S. PATENT DOCUMENTS 8,921,118 B2 12/2014 Siegel et al.
10,772,998 B2 * 9/2020 Luxon .................. A61M 1/742
(Continued)

FOREIGN PATENT DOCUMENTS

WO 2009121041 A2 10/2009
WO WO-2015105916 A1 * 7/2015 ............. A61B 5/208

OTHER PUBLICATIONS

Ballerini et al., "Patterned paper and alternative materials as substrates for low-cost microfluidic diagnostics", article, Published online: May 22, 2012, 20 total pages.
(Continued)

*Primary Examiner* — Rebecca E Eisenberg
*Assistant Examiner* — Kate Elizabeth Strachan
(74) *Attorney, Agent, or Firm* — TAFT STETTINIUS HOLLISTER LLP; Ryan O. White; Derek B. Lavender

(57) ABSTRACT

A urinary catheter having a sensor or indicator affixed therein in a location that will be in the flow of urine when catheter is in use. The indicator comprises an electrolytic wicking material having an anode and a cathode thereon separated across the gap. The wicking material may be paper. The indicator further includes an output transducer positioned and connected relative to the anode and cathode such that a circuit which energizes the output transducer is created when urine flows. The indicator is configured to generate an output signal received at a remote location so that a medical practitioner can monitor proper usage of the catheter. There may be multiple anode/cathode pairs connected in series or parallel to increase voltage or current. Also, a capacitor and/or an antenna may be provided for the output transducer to boost the output signal.

22 Claims, 8 Drawing Sheets

(52) U.S. Cl.
CPC ............... *A61M 2205/3334* (2013.01); *A61M 2210/1085* (2013.01); *A61M 2210/1089* (2013.01)

(58) Field of Classification Search
CPC .. A61M 2202/0496; A61M 2205/3327; A61M 27/00; A61B 5/208; A61B 5/6852; A61B 2560/028; A61B 5/4833; A61B 5/0002; A61B 5/201; A61B 2562/0217; H01Q 1/273; H01Q 1/2225
See application file for complete search history.

(56) References Cited

U.S. PATENT DOCUMENTS

| | | |
|---|---|---|
| 2005/0084737 A1 | 4/2005 | Wine et al. |
| 2009/0092882 A1 | 4/2009 | Kjeang et al. |
| 2011/0271424 A1 | 11/2011 | Cavalier |
| 2012/0288961 A1 | 11/2012 | Yaher et al. |
| 2013/0041234 A1 | 2/2013 | Grinstein et al. |
| 2016/0120455 A1 | 5/2016 | Pop et al. |
| 2017/0113000 A1 | 4/2017 | Tobescu et al. |
| 2017/0136209 A1 | 5/2017 | Burnett et al. |
| 2018/0043361 A1* | 2/2018 | Sabate Vizcarra .... G01J 1/0403 |
| 2018/0368744 A1 | 12/2018 | Cahan et al. |
| 2018/0368745 A1 | 12/2018 | Cahan et al. |

OTHER PUBLICATIONS

Esquivel et al., "Fuel cell-powered microfluidic platform for lab-on-a-chip applications: Integration into an autonomous amperometric sensing device", Electronic Supplementary Information, Electronic Supplementary Material (ESI) for Lab on a Chip, published Sep. 2012, 2 pages.

United States Patent and Trademark Office, Final Office Action for U.S. Appl. No. 15/300,521, mail date Dec. 10, 2018, 29 total pages.

* cited by examiner

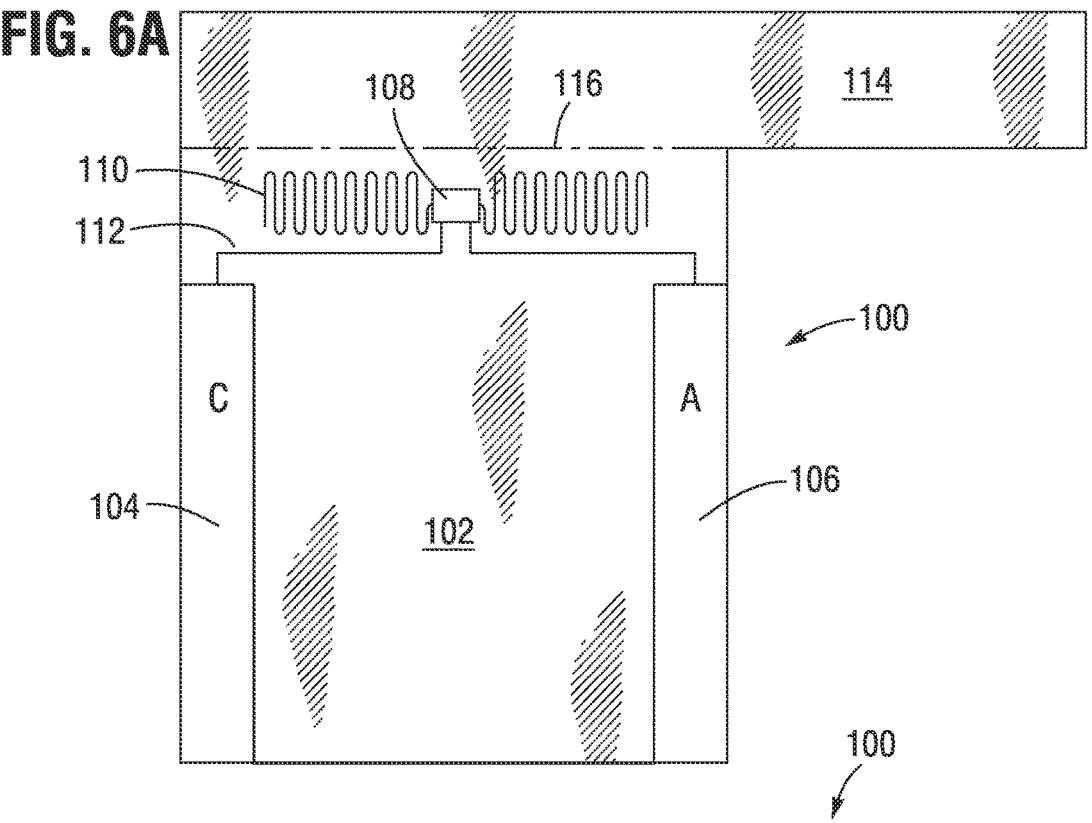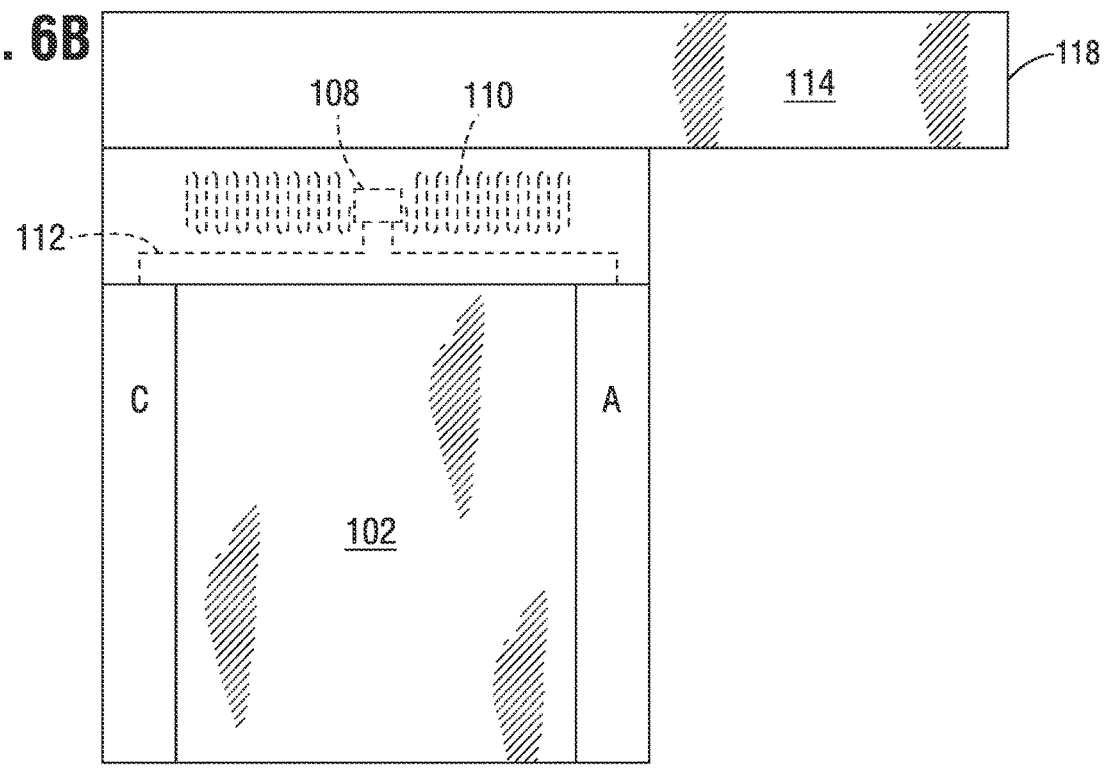

METHODS OF MONITORING URINARY CATHETER USAGE

RELATED APPLICATIONS

The present application is a continuation-in-part of U.S. patent application Ser. No. 17/097,941, filed Nov. 13, 2020, which claims priority to U.S. Provisional Application No. 62/936,994 filed Nov. 18, 2018 the contents of which are expressly incorporated herein.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

FIELD

The present invention relates to a urinary catheter and, more particularly, to a smart urinary catheter having a flow indicator built-in to sense when the catheter has been used.

BACKGROUND

The urinary system contains two kidneys, two ureters, the bladder and the urethra. The kidneys filter the blood and produce urine. The urine travels from the kidneys down the ureters and into the bladder, where it is stored until emptied during urination. The urethra is the tube that empties the urine out of the body. When the bladder is full, the burn sends a signal down the spinal cord to the bladder, causing it to empty. Unfortunately, spinal cord injuries such as spina bifida and certain other similar conditions interfere with these signals.

There are an estimated 12,000 spinal cord injuries every year in the United States. More than a quarter of a million Americans are currently living with spinal cord injuries. The largest proportion of spinal cord injuries (36.5%) occurs during car accidents; more than a quarter are the result of falls; and the rest are due to acts of violence (primarily gunshot wounds), sporting accidents, and other less common causes. The average age at injury has risen and is now 42.6 years. 80 percent of spinal cord injury patients are men.

Most spinal cord injuries affect bladder and bowel functions because the nerves that control the involved organs originate in the segments near the lower end of the spinal cord and lose normal brain input. Although the kidneys continue to produce urine, bladder control may be lost, and the risk of bladder and urinary tract infections increases.

When people are unable to empty their bladder on their own, they are at risk for urinary tract infections, as well as incontinence or involuntary loss of urine. When urine stays in the bladder and is not emptied, bacteria can grow, causing infections which can lead to illness. Research has shown that intermittent self-catheterization helps reduce urinary tract infections, control urinary leakage (incontinence) and prevent urinary tract damage.

Patients are sometimes prescribed urinary catheters but fail to use or misuse them for a variety of reasons, such as inconvenience, embarrassment, forgetfulness, and simple stubbornness, among many. Consequently, there is a need for a system to ensure compliance.

SUMMARY OF THE INVENTION

The present application discloses a number of intermittent urinary catheters each incorporating a sensor or indicator that registers usage of the catheter. The indicators are inexpensive so as not to unduly increase the cost of relatively inexpensive urinary catheters, and monitor one-time usage of the catheters, which are universally disposable. The indicators incorporate an electrolytic cell energized by urine flow that powers an electric signaling device. The signaling device includes a small transmitting antenna which interacts with a local device such as a smart phone. The signaling device possesses a unique signature for that particular urinary catheter which has been assigned to the user. In this way, the local device collects usage information for that user and can then forward the aggregate information to a medical provider for analysis.

The present application provides a "smart" urinary drainage catheter that incorporates a very low-cost sensor or indicator powered by a urine battery. The indicator would link to a smart phone and would allow tracking of catheter use to ensure patient compliance. Each catheter would have a unique indicator (serialized) and the catheters would be assigned to a user at time of sale. When a user drained their bladder, the indicator would activate and signal that it was being used. A medical professional could then track usage history and intervene if there were signs of noncompliance (e.g., not draining frequently enough, reuse of catheters etc.).

A method of monitoring urinary catheter usage is disclosed which, comprises providing a urinary catheter having a flexible catheter tube with a length and diameter sized for introduction and advancement through a user's urethra to the user's bladder. The urinary catheter has a flow indicator affixed therein so as to be exposed to urine, the flow indicator comprising a porous substrate configured to pass an electrolytic ion flow between an anode and cathode pair thereon when wetted. The flow indicator further includes an output transducer connected to the anode and cathode such that an electrical current which energizes the output transducer is created when urine flows through the catheter and wets the indicator. The output transducer is configured to generate an output signal adapted to be received at a remote location, and the method includes monitoring the output signal at the remote location. Desirably, the output transducer has a unique signature for that particular urinary catheter and is configured to generate an output signal indicating when urine flows and the unique signal, and the method involves monitoring the output signals of a plurality of the urinary catheters.

The method may include associating unique signatures for a plurality of urinary catheters to individuals. The method may also involve collecting and analyzing output signals generated by multiple urinary catheters associated with a single individual to monitor health indicators and usage compliance. Alternatively, the steps of collecting and analyzing output signals may be for manufacturing or marketing purposes.

In the afore-described devices or methods, the flow indicator output transducer may be positioned and connected to the anode and cathode with connecting wires or current carrying pathways on the substrate. Further, the urinary catheter may have an outlet comprising a flared funnel, and the flow indicator is affixed within the funnel or within the lumen of the tube. Preferably, the output transducer includes an antenna connected to amplify the output signal, and the output transducer and antenna are 3D printed or screen printed onto the porous substrate. In one form, the output transducer includes a capacitor to store up and discharge power to an antenna. There may be a plurality of anode and cathode pairs on the substrate connected in series or parallel.

The porous substrate may have an expanded configuration for fabrication convertible to a compacted configuration which is affixed within the urinary catheter. The porous substrate may be made of paper or electrolyte-infused paper so as to form a transfer path through which ions may flow, and the anode and cathode are formed by materials printed on the paper. The expanded configuration may include an insulated strip foldable over the output transducer.

One version of the smart catheter would only track usage but as sensors became more available other items could be tracked such as volume drained, flow rate, the presence of bacteria above critical level (infection), mineral levels, and/or hydration level.

BRIEF DESCRIPTION OF THE DRAWINGS

FIG. 6A is a plan view of an alternative flow indicator that may be utilized in a urinary catheter as described herein, and FIG. 6B is a view showing the alternative indicator after folding down a top flap to cover electronics thereon;

DETAILED DESCRIPTION OF A PREFERRED EMBODIMENT

The present application provides a "smart" urinary drainage catheter that incorporates a very low-cost sensor or indicator powered by a urine activated battery. The indicator would link to a smart phone allow tracking of catheter use to ensure patient compliance.

Figure 1:
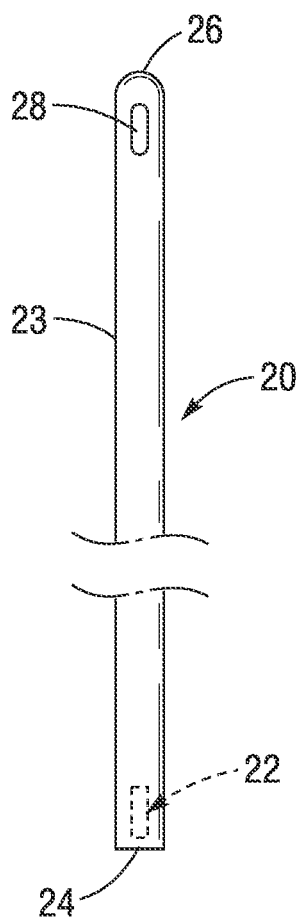
FIG. 1 is a schematic illustration of a urinary catheter tube having a sensor or indicator affixed therein.

FIG. 1 is a schematic illustration of a urinary catheter 20 having a sensor or indicator 22 affixed therein. The indicator is affixed inside a lumen of a catheter tube 23, such as adjacent a proximal end 24. The catheter tube 24 may be part of a number of different types of urinary catheters, male or female, drainage or collecting, such as those sold by Cure Medical, LLC of Newport Beach, CA Urinary catheters 20 of this type have a rounded distal tip 26 that may be lubricated and inserted into the urethra, wherein the user advances the tube 20 until the distal tip enters the bladder. Urine then flows into one or more openings or eyelets 28 adjacent the distal tip 26 and proximally through the lumen of the tube 23. The proximal end 24 defines an outlet that may be held by the user over a toilet with the like, or may be sealed within a collection bag (not shown), depending on the type of urinary catheter.

Figure 2:
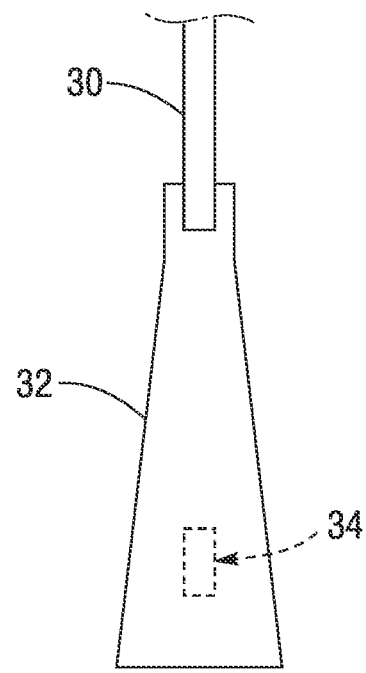
FIG. 2 is a schematic illustration of a urinary catheter tube having a proximal funnel with a sensor or indicator affixed therein.

FIG. 2 shows a portion of a urinary catheter tube 30 having a proximal end leading to a flared outlet funnel 32 with a sensor or indicator 34 affixed therein. The funnel 32 is often used in drainage catheters to provide a convenient spout of sorts for directing the urine into a toilet. Also, widened proximal ends on catheters such as the funnel 32 are used within sterile collection bags to prevent the entire catheter from being removed from the bag.

Figure 3C:
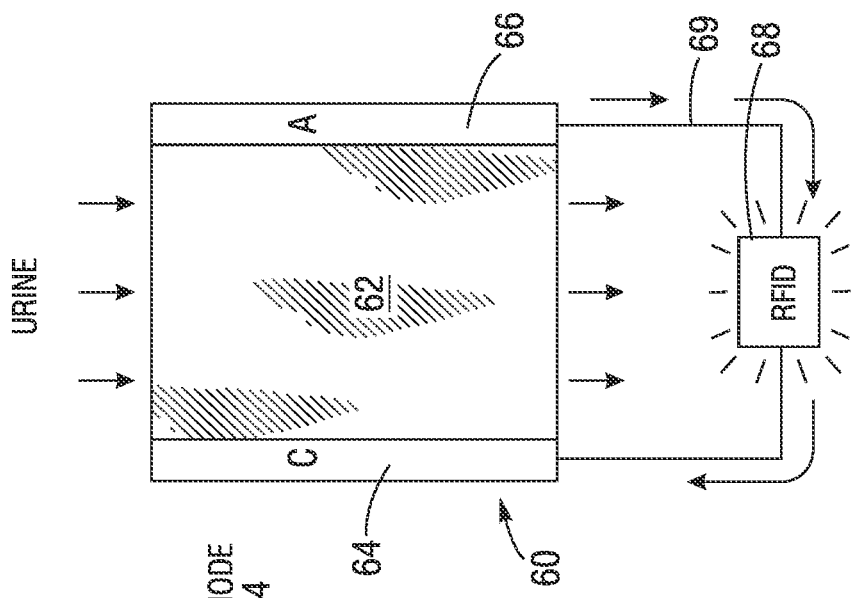
FIGS. 3A-3C are schematic views of different embodiments of a sensor or indicator that may be mounted within a urinary catheter, in accordance with the present application.
Figure 3B:
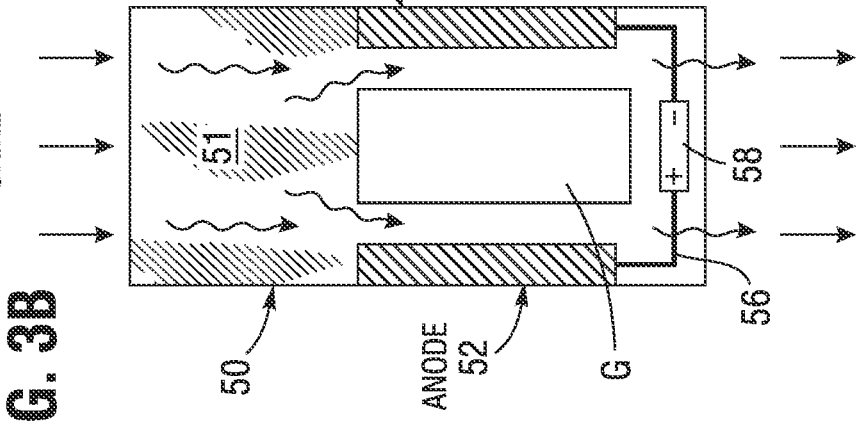
Figure 3A:
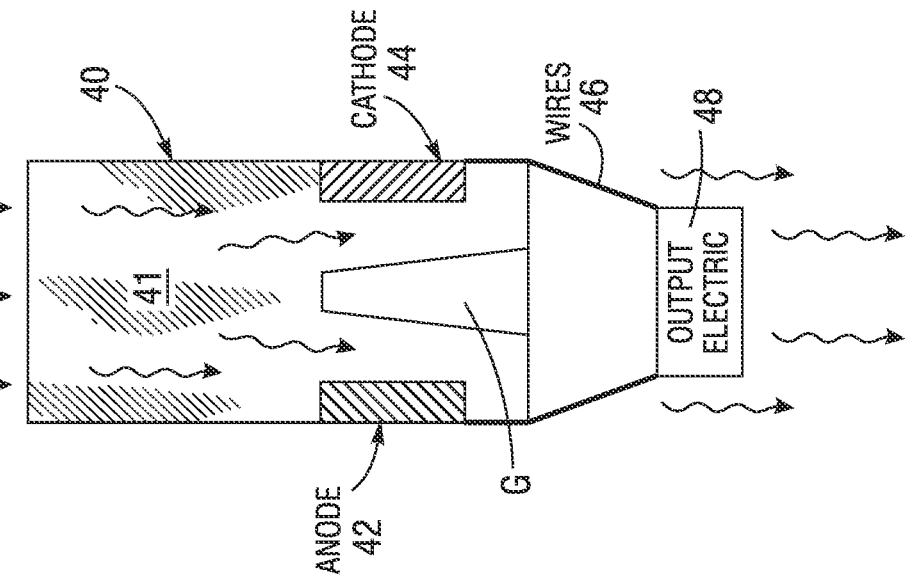

FIG. 3A is a schematic view of one embodiment of a sensor or indicator 40 that may be placed within a catheter, such as shown in FIGS. 1 and 2. The indicator comprises a porous electrolytic material or substrate 41 doped with anodic and cathodic material to form an anode 42 and a cathode 44 spaced apart across a gap G.

The electrolytic substrate 41 allows for fluid wicking. In a preferred embodiment, the electrolytic substrate 41 is paper or other such wicking material which when wetted with urine creates an ion flow. The infusion of sodium hydroxide, potassium hydroxide or the like to form electrolyte infused paper may enhance the ability of the substrate to transfer ions. The urine wets or saturates the substrate 41 which allows for chemical reactions to occur at both the cathode and electrode. If the cathode and anode are connected via a conductive path with an electrical load a current will be generated. This would make a complete circuit so current could flow.

With respect to the microstructure of a porous electrode substrate, it is porous and facilitates liquid and/or gaseous flow of reactant through the pores when wetted. Also, the solid substrate may be treated with a salt, acid or base such that it will more efficiently transfer ions when wetted with urine. The porosity should be relatively constant spatially to facilitate uniform flow distribution. Porous materials include, but are not limited to fibrous carbons, felts, papers, cloths, silica, gels, foams, sponges, ceramics, filters, meshes, wicks, membranes, polymers, and metal-organic frameworks.

The anodic material can be selected from the group consisting of zinc, lithium, aluminum, or magnesium. The cathodic material may be selected from a group consisting of carbon nickel, cobalt, or manganese. In a preferred embodiment, the anodic material is aluminum, and the cathodic material is nickel. The anodic and cathodic materials are preferably printed on electrolyte-infused paper.

One source of materials that can be used for the indicators of the present application is US 2018/0043361 to Vizcarra, the contents of which are expressly incorporated herein.

The indicator 40 produces an output signal when urine flows through or otherwise saturates the electrolytic substrate 41. When urine contacts the anode 42 and cathode 44, an ion flow is created which energizes an electrical output transducer 48 via current carrying pathways. More particularly, a pair of wires 46 are electrically connected to the anode 42 and cathode 44 and connect to opposite poles of the output transducer 48, which may be physically separated from the substrate 41 as shown. The electrolytic urine saturates the electrolytic substrate 41 and ion begins to flow between the anode 42 and cathode 44. Ions pass through the electrolyte substrate 41 and drive electron flow in (i.e., energize) the output transducer 48 through the wires 46. The gap G may help reduce direct ion flow between the anode 42 and cathode 44 and thus focus flow to the wires 46.

The current carrying pathways (e.g., wires 46) may be partly printed or deposited through the substrate 41, or along edges thereof as shown. One technique is to deposit carbon ink along the edges which acts like a wire 46 to create current carrying pathways.

The output transducer 48 may be a variety of devices, but preferably comprises an antenna connected to amplify an output of the output transducer 48 and send a signal to a capture device (e.g., smartphone etc.). Further, the output transducer 48 may incorporate a capacitor to store up a charge over time (e.g., milliseconds) and then discharge suddenly to provide a quick burst of power and amplify the output signal. The indicator 40 does not collect the urine—it just lets it pass through. The signal sent by the output transducer 48 provides an indication that the catheter has been in use. The signal may be received and tracked by a medical practitioner or recording device monitored by the medical practitioner to keep track of when and how often the urinary catheter has been used. Moreover, the signal includes a distinctive signature (e.g., serial number) assigned to a user at time of sale or delivery of the catheter which enables the recipient of the signal to track which catheter and presumptively which user has been activated. This enables the medical practitioner to monitor proper compliance with the catheter usage. In addition, the indicator resets a given time after use as it dries in the absence of urine. If the device is used again, the output transducer 48 generates another signal which is also received by the medical practitioner, indicating that the catheter has been improperly used twice.

FIG. 3B is a schematic view of a second embodiment of a sensor or indicator 50 that may be mounted within a catheter, such as seen in FIGS. 1 and 2. In this embodiment, an electrolytic substrate 51 is formed with an open space forming a gap G between the anode 52 and cathode 54. Instead of wires, the electrical output transducer 58 is printed or otherwise affixed to the electrolytic substrate 51 at one end of the gap G. That is, the output transducer 58 is 3D printed or screen printed onto the electrolytic substrate 51 along a portion positioned between the anode 52 and cathode 54 so as to be in an ion flow therebetween. The output transducer 58 has poles on opposite ends which complete the circuit generated by ions flowing between the anode 54 and cathode 54. Current carrying pathways 56 that may be printed or deposited on the substrate 51 provide an enhanced electron flow pathway to opposite poles of the output transducer 58 from the anode 52 and cathode 54, respectively.

The output transducer 58 may be an RFID chip which can be 3D printed, screen printed, or otherwise adhered to the substrate 51. The transducer 58 has a central chip bonded to the substrate 51, such as paper, which chip can be programmed with product information.

FIG. 3C is a further embodiment of a flow indicator 60 that includes a porous electrolytic substrate 62 having a cathode 64 and an anode 66 printed on opposite lateral sides. The substrate 62 is mounted within a urinary catheter so that urine saturates the area of the substrate 62 separating the cathode 64 and anode 66, thus creating an electrolytic ion flow. An output transducer 68 such as a radio-frequency identification (RFID) chip 68 is connected in series to both the cathode 64 and anode 66 via wires 69, and is otherwise separated from substrate 62. Alternatively, the RFID chip 68 may be printed on the substrate 62, such as the output transducer 58 of FIG. 3B. In a like manner the wires can be current carrying pathways printed on the paper using carbon ink. When urine flows and saturates the substrate 62, the resulting ion flow energizes the RFID chip 68 which produces an output signal that can be transmitted to a local device such as a smart phone.

In a preferred embodiment, the indicator is only a sensor. If more information is desired, the sensor may analyze the urine for volume drained, flow rate, the presence of bacteria above critical level (infection), mineral levels, and/or hydration level.

Figure 4:
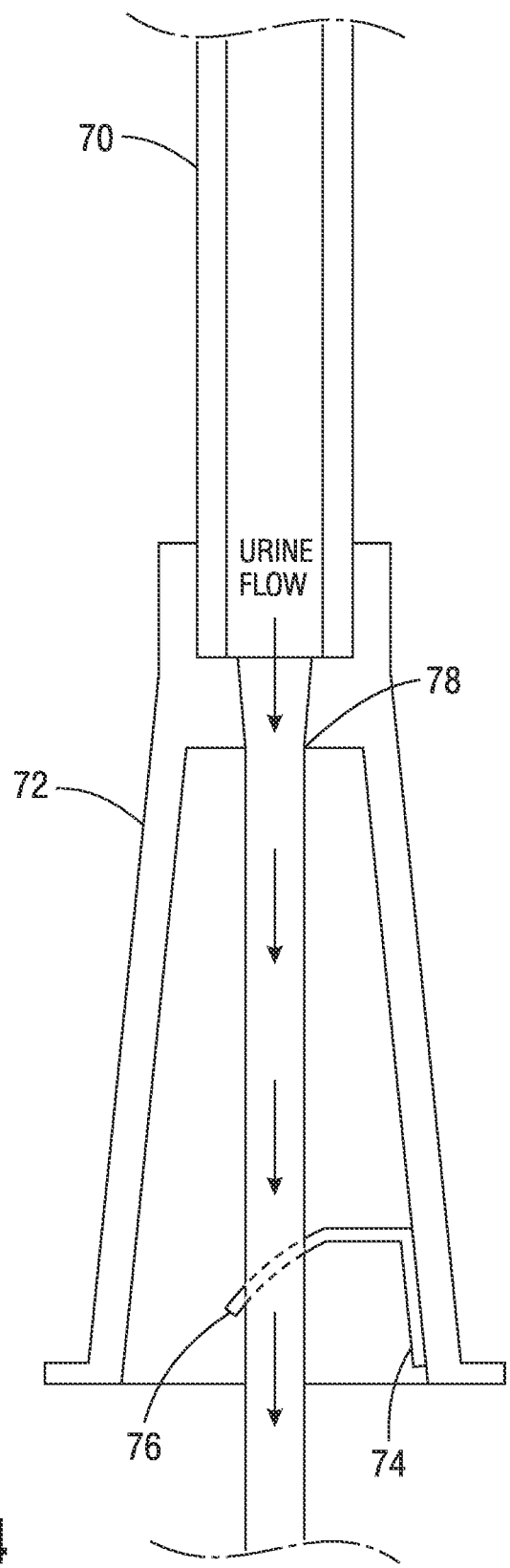
FIG. 4 is a schematic view of a third embodiment of a paper sensor or indicator within a urinary catheter in which the sensor is mounted so as to stay dry.

FIG. 4 shows an embodiment that lets the anode and cathode contact urine but keeps the electrical output portion of the indicator dry and away from an electrical short condition. In this embodiment, a catheter tube 70 has a proximal end leading to a flared outlet funnel 72. The funnel 72 has an inner wall that tapers gradually wider and to which a first portion 74 of the indicator is attached and on which an output transducer (not shown) may be located. The indicator may be constructed as disclosed above with respect to FIGS. 3A-3C.

A second portion 76 of the indicator is cantilevered laterally across a centerline of the funnel 72. The second portion 76 lies in the path of urine flow through the catheter, which flow is preferably concentrated by a sharp edge 78 at the inlet of the funnel 72. Keeping the first portion 74 of the indicator with the output transducer out of the direct flow may prevent short circuits.

Figure 5A:
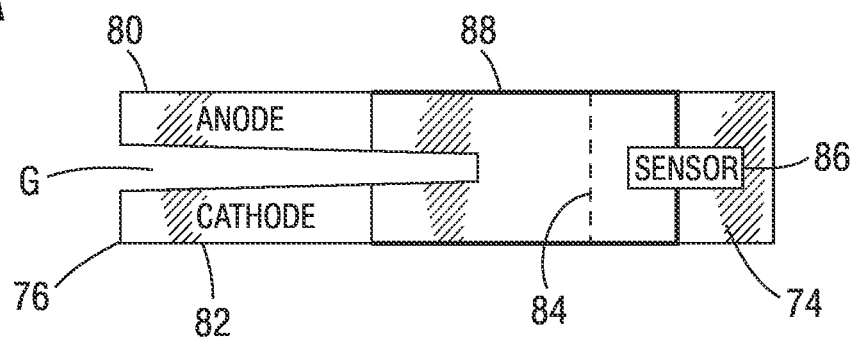
FIG. 5A is a plan view of the paper indicator of FIG. 4 before folding.
Figure 5B:
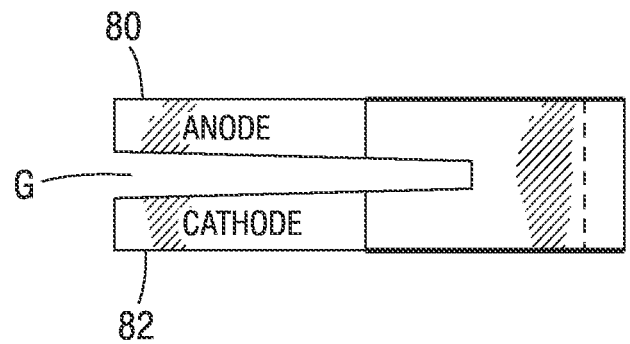
FIGS. 5B and 5C are views of the paper indicator after folding.
Figure 5C:
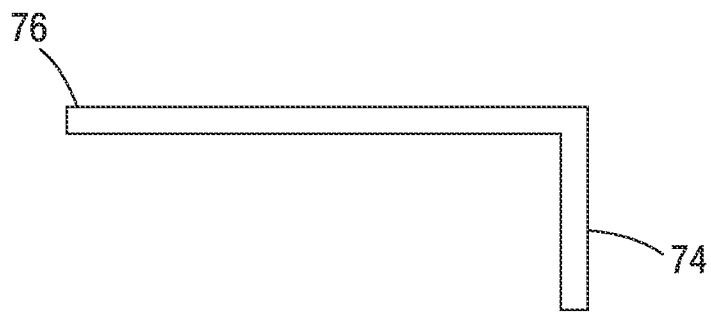

FIG. 5A is a plan view of the paper indicator of FIG. 4 before folding, and FIGS. 5B and 5C are views of the paper indicator after folding. The indicator preferably has a bifurcated second portion 76 separated by a gap G. Anodic and cathodic material are printed or otherwise adhered to the electrolytic material of the indicator so as to form an anode 80 and cathode 82 across the gap G. A fold line 84 separates the first portion 74 from the second portion 76, such that the indicator can easily be adhered to the inside of the funnel 72 when bent as shown in FIG. 5C. An output transducer or sensor 86 is positioned somewhere on the second portion 76 and functions similar to those described above. Wires 88 extend between opposite poles of the output transducer 86 and the respective anode 80 and cathode 82. The wires 88 may be 3D printed or screen printed, or deposited along the edges of the indicator as shown and provide current carrying pathways.

The gap G may help reduce direct ion flow between the anode 80 and cathode 82 and thus focus electron flow to the wires 88. The gap G also facilitates urine flow past the indicator.

FIG. 6A is a plan view of an alternative flow or usage indicator 100 that may be utilized in a urinary catheter as described herein, and FIG. 6B is a view showing the alternative indicator after folding down a top flap to cover electronics thereon. The usage indicator 100 is once again primarily formed of a porous substrate 102 which is generally rectangular. A printed or deposited cathode 104 and anode 106 are provided on opposite lateral side edges across an area of the substrate 102. An output transducer 108 on the substrate 102 is positioned between the cathode 104 and anode 106; the transducer having an antenna 110 extending outward therefrom also mounted on the substrate 102. The antenna 110 is connected to amplify an output of the output transducer 108 and send a signal to a remote device such as a smartphone. Wires 112 may connect the transducer 108 to the cathode 104 and anode 106, or the substrate 102 may be printed with conductive material paths. As mentioned above, the transducer 108 may be an RFID chip which is 3D printed or screen-printed on the substrate 102, with a chip programmed with product and/or customer information. The output transducer 108 may also incorporate a capacitor to store up a charge over time (e.g., milliseconds) and then discharge suddenly to provide a quick burst of power and amplify the signal.

The usage indicator 100 also has a rectangular fold strip 114 contiguous with and made of the same material as the substrate 102, and separated from the primary rectangular area at a fold line 116. The strip 114 may be folded downward at the fold line 116 so as to cover the transducer 108, antenna 110 and wires 112, as seen in FIG. 6B. Although the strip 114 is desirably formed of the same material as the substrate 102, it is preferably not impregnated with electrolytic substance and is instead insulating. The insulating fold strip may be treated to improve its ability to retain its insulating character. The treating material may be a wax, polymer or hydrophobic material. By folding the insulating strip 114 over the electronics 108, 110, 112, the circuit is physically protected and electrically insulated.

Figure 6C:
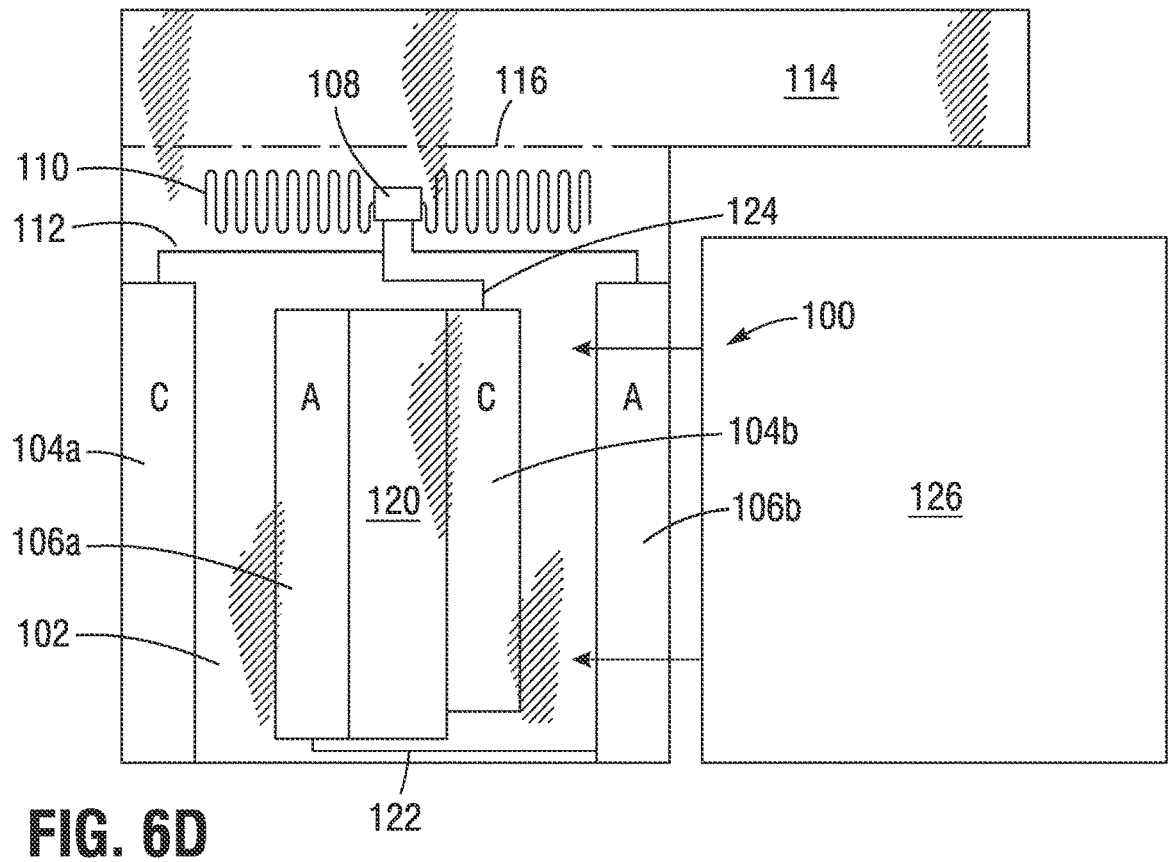
FIGS. 6C and 6D are plan views of flow indicators similar to that of FIGS. 6A/6B but with multiple anodes and cathodes in parallel and series configuration, respectively.
Figure 6D:
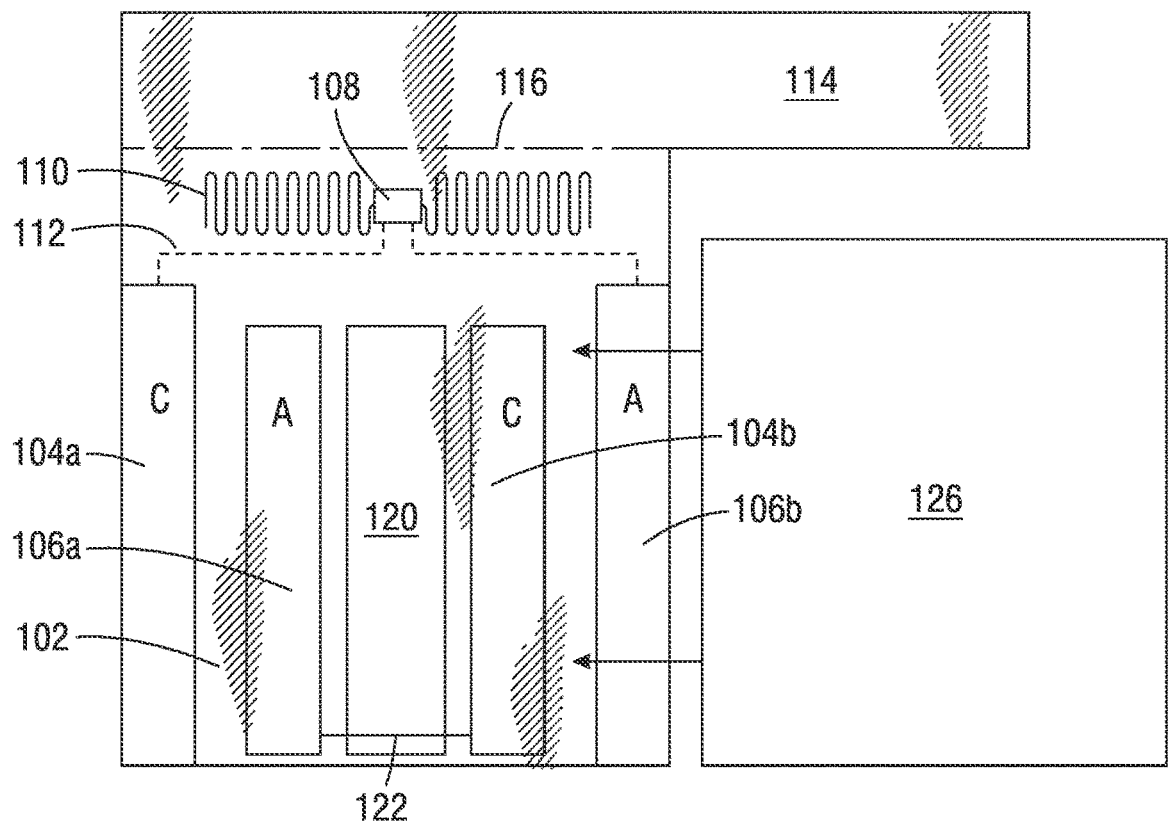

FIGS. 6C and 6D are plan views of flow indicators 100 similar to that of FIGS. 6A/6B but with multiple anodes and cathodes in parallel and series configuration, respectively. Ionic flow circuits fairly consistently provide 1.5 volts, such that connecting anode/cathode pairs in series increases the voltage to 3, 6, even 9 volts, etc. Similarly, the current in any of the flow indicators 100 described herein may me increased by connecting anode/cathode pairs in parallel. Dual anode/cathode pairs are shown in FIGS. 6C and 6D to increase the current and voltage, respectively, though more than two may be provided depending on the need.

In particular, FIG. 6C shows a substrate 102 on which first and second cathodes 104a, 104b, and first and second anodes 106a, 106b are printed or deposited. Ions flow between the first cathode 104a and first anode 106a, and between the second cathode 104b and second anode 106b. A strip of insulation 120 on the substrate 102 is imposed between the two cathode/anode pairs to prevent shorting. The cathodes 104 and anodes 106 are connected in parallel to an output transducer 108 via a plurality of wires 122, 124 to increase current capacity of the flow indicator. The output transducer 108 may incorporate a capacitor to store up a charge over time (e.g., milliseconds) and then discharge suddenly to provide a quick jolt of power and amplify the signal. Furthermore, an insulating panel 126 may be secured over the top of the substrate 102 which further prevents shorting and increases efficiency.

FIG. 6D shows a substrate 102 on which first and second cathodes 104a, 104b, and first and second anodes 106a, 106b are again printed or deposited. Ions flow between the first cathode 104a and first anode 106a, and between the second cathode 104b and second anode 106b. A strip of insulation 120 on the substrate 102 is imposed between the two cathode/anode pairs to prevent shorting. The cathodes 104 and anodes 106 are connected in series to an output transducer 108 via wires 112, 122 to increase voltage capacity of the flow indicator. As mentioned above, the output transducer 108 may again incorporate a capacitor to store up a charge over time and then discharge suddenly to provide a quick burst of power and amplify the signal. Furthermore, an insulating panel 126 may be secured over the top of the substrate 102 which further prevents shorting and increases efficiency.

Figure 7:
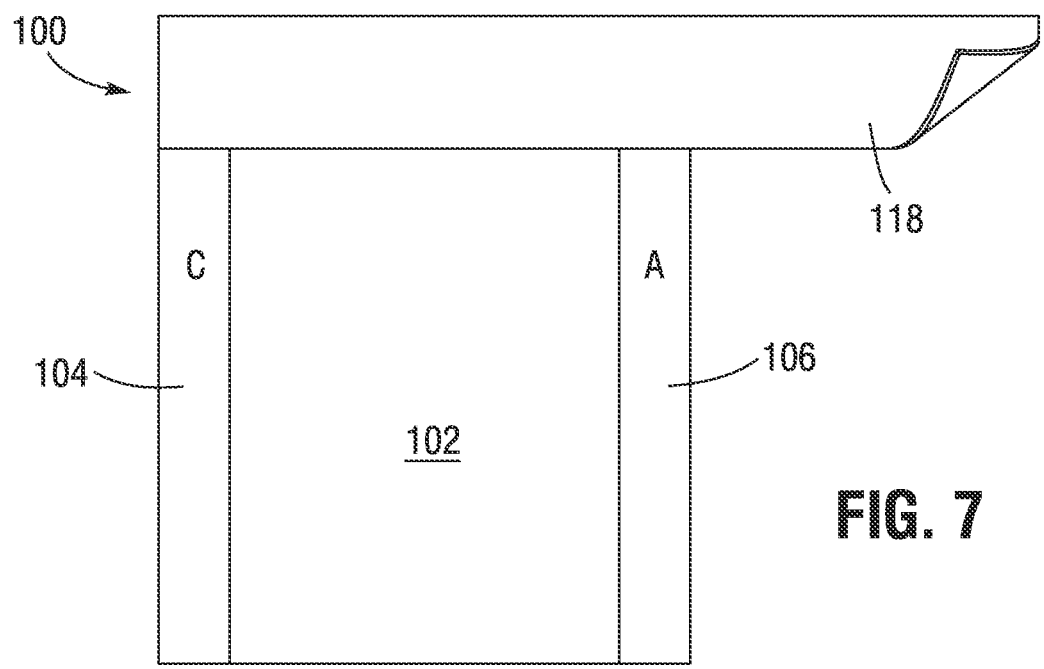
FIG. 7 is a plan view of the assembled alternative flow indicator.

FIG. 7 is a plan view of the assembled alternative usage indicator 100 indicating a lateral tab 118 that is formed after folding the strip 114 over. As will be described, the indicator 100 may be compacted in various ways and the tab 118 then used to hold the assembly in a compact form so that it may be inserted into a urinary catheter.

Figure 8A:
FIGS. 8A/8B, 9A/9B, and 10A/10B are elevational and top plan views of the assembled alternative flow indicator of FIG. 7 after having been compacted in various ways.
Figure 8B:
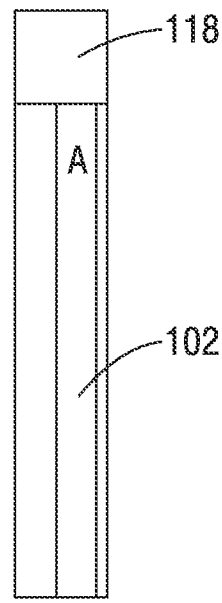

FIGS. 8A/8B, 9A/9B, and 10A/10B are elevational and top plan views of the assembled alternative usage indicator 100 of FIG. 7 after having been compacted in various ways. First, FIGS. 8A and 8B show the substrate 102 rolled up into a spiral with the tab 118 then used to secure a top portion thereof. The tab 118 may have adhesive or other such fastener to hold the rolled tube together.

Figure 9A:
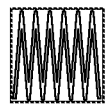
Figure 9B:
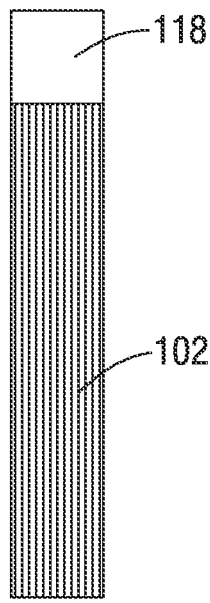

FIGS. 9A and 9B show the substrate 102 folded into a zig-zag or accordion shape. Again, the lateral tab 118 is wrapped around the top end and secures the assembly in the compact state.

Figure 10A:
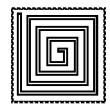
Figure 10B:
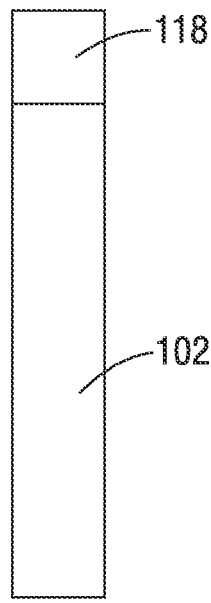

Finally, FIGS. 10A and 10B shows substrate 102 rolled up using a square or rectangular fold, again with the lateral tab 118 securing the top end to maintain the compact shape. Each of the compacted embodiments thus has the majority of the substrate 102 with the anode and cathode thereon folded but not enclosed, and a top portion with the electronics including the transducer 108, antenna 110 and wires 112 covered by the closure tab 118. Once again, the tab 118 is formed by a portion of the insulating strip 114 which both physically and electrically protects the components therein.

Figure 11:
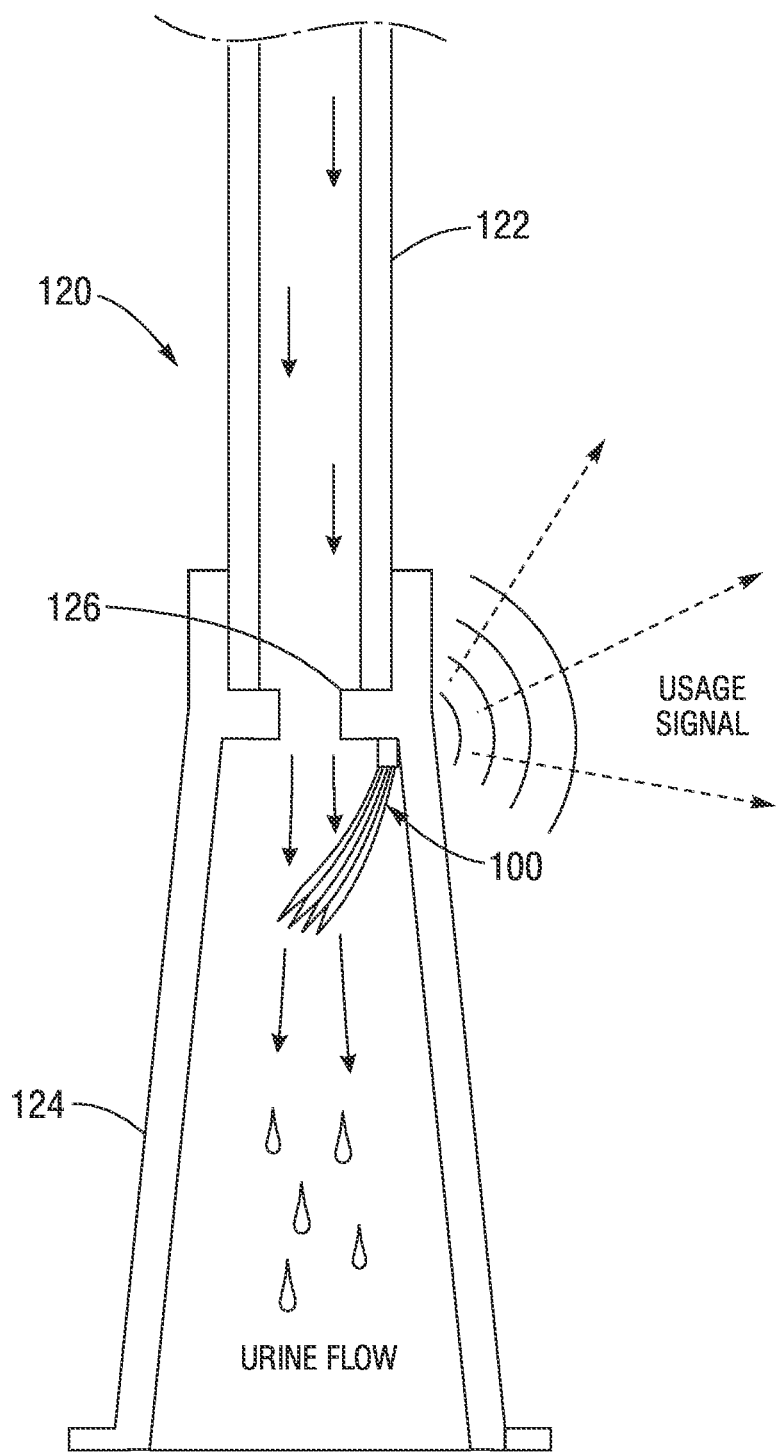
FIG. 11 is a schematic view of the alternative flow indicator within a urinary catheter in which the sensor is mounted so as to stay dry.

FIG. 11 is a schematic view of the alternative usage indicator 100 mounted within a urinary catheter 120 in which the sensor is mounted so as to stay dry. More particularly, the catheter 120 again has a tube 122 that connects at a proximal end to an outlet funnel 124. The funnel may include a flange 126 which narrows the opening from the lumen of the catheter tube 122 to the lumen of the funnel 124. The usage indicator 100 may be secured within the funnel just beyond or downstream from the flange 126, so that the upstream or top end including the electronics 108, 110, 112 wrapped up in the insulating tab 118 is positioned out of the direct urine flow. This enables the lower portion including the substrate 102 having the cathode and anode 104, 106 to hang down so as to be easily wetted by the urine flow. As explained above, once the urine saturates the substrate 102, an electrolytic circuit is created which energizes the transducer 108 and broadcasts the usage signal via the antenna 110.

The various flow indicators described herein may be incorporated into a monitoring system and methodology for tracking usage and encouraging compliance with proper procedures. Because the flow indicators do not significantly increase the cost of relatively inexpensive and disposable urinary catheters, and function autonomously, they may be widely adopted without inconveniencing the user. The signaling devices within the indicators have unique signatures for that particular urinary catheter which may be assigned to each user so that usage information for that user and can be forwarded automatically to a medical provider for analysis.

One method of using the "smart" urinary drainage catheter involves linking the output signal to a smart phone app which is then readily available to a medical professional. Tracking of catheter use to monitor health indicators and ensure patient compliance with proper usage is one benefit. For example, when a user urinates, the indicator activates and signals that it has been used. A medical professional can then track usage history and intervene if there are signs of difficulty or noncompliance, such as not urinating frequently enough, or if a single catheter is reused, etc. The simplest version of a smart catheter disclosed herein only tracks usage. However, as different sensors become more available and are incorporated into the smart catheter, other parameters could be tracked, such as volume drained, volume flow rate, the presence of bacteria above critical level (infection), mineral levels, and/or hydration level.

Other tangential benefits of tracking usage are purely for commercial purposes. That is, flow indicators may be coded for different types of catheters such that the aggregate usage of those different catheters may be tracked. Knowing how many catheters are being used may be helpful for manufacturing and marketing purposes. Also, geographic and/or demographic information may be included in any unique signature attributed to the flow indicators to enable greater understanding of usage over populations and areas.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments.

It is claimed:

1. A method of monitoring urinary catheter usage, comprising:
    a) providing a urinary catheter having a flexible catheter tube with a length and diameter sized for introduction and advancement through a user's urethra to the user's bladder, the urinary catheter having a flow indicator affixed therein so as to be exposed to urine, the flow indicator comprising a porous substrate configured to pass an electrolytic ion flow between an anode and cathode pair thereon when wetted, the flow indicator further including an output transducer connected to the anode and cathode such that an electrical current which energizes the output transducer is created when urine flows through the catheter and wets the indicator, the output transducer being configured to generate an output signal adapted to be received at a remote location;
    b) monitoring the output signal at the remote location.

2. The method of claim 1, wherein the flow indicator output transducer is positioned and connected to the anode and cathode with connecting wires or current carrying pathways on the substrate.

3. The method of claim 1, wherein the urinary catheter has an outlet comprising a flared funnel, and the flow indicator is affixed within the funnel or within the lumen of the tube.

4. The method of claim 1, wherein the porous substrate has an expanded configuration for fabrication convertible to a compacted configuration which is affixed within the urinary catheter.

5. The method of claim 1, wherein the output transducer has a unique signature for that particular urinary catheter, and the method includes associating unique signatures for a plurality of urinary catheters to individuals.

6. The method of claim 5, wherein the method collecting and analyzing output signals generated by multiple urinary catheters associated with a single individual to monitor health indicators and usage compliance.

7. The method of claim 5, wherein the method collecting and analyzing output signals generated by multiple urinary catheters associated with multiple individuals for manufacturing and marketing purposes.

8. The method of claim 1, wherein the porous substrate is made of paper or electrolyte-infused paper so as to form a transfer path through which ions may flow, and the anode and cathode are formed by materials printed on the paper.

9. The method of claim 1, wherein the output transducer includes an antenna connected to amplify the output signal, and the output transducer and antenna are 3D printed or screen printed onto the porous substrate.

10. The method of claim 1, wherein the output transducer includes a capacitor to store up and discharge power to an antenna.

11. The method of claim 1, wherein there are a plurality of anode and cathode pairs on the substrate connected in series or parallel.

12. A method of monitoring urinary catheter usage, comprising:
    a) providing a urinary catheter having a flexible catheter tube with a length and diameter sized for introduction and advancement through a user's urethra to the user's bladder, the urinary catheter having a flow indicator affixed therein so as to be exposed to urine, the flow indicator comprising a porous substrate configured to pass an electrolytic ion flow between an anode and cathode pair thereon when wetted, the flow indicator further including an output transducer connected to the anode and cathode such that an electrical current which energizes the output transducer is created when urine flows through the catheter and wets the indicator, the output transducer having a unique signature for that particular urinary catheter and being configured to generate an output signal indicating when urine flows and the unique signal;
    b) monitoring the output signals of a plurality of the urinary catheters.

13. The method of claim 12, wherein the flow indicator output transducer is positioned and connected to the anode and cathode with connecting wires or current carrying pathways on the substrate.

14. The method of claim 12, wherein the urinary catheter has an outlet comprising a flared funnel, and the flow indicator is affixed within the funnel or within the lumen of the tube.

15. The method of claim 12, wherein the porous substrate has an expanded configuration for fabrication convertible to a compacted configuration which is affixed within the urinary catheter.

16. The method of claim 15, wherein the expanded configuration includes an insulated strip foldable over the output transducer.

17. The method of claim 12, wherein the method includes associating unique signatures for a plurality of urinary catheters to individuals, and collecting and analyzing output signals generated by multiple urinary catheters associated with a single individual to monitor health indicators and usage compliance.

18. The method of claim 12, wherein the method includes associating unique signatures for a plurality of urinary catheters to individuals, and collecting and analyzing output signals generated by multiple urinary catheters associated with multiple individuals for manufacturing or marketing purposes.

19. The method of claim 12, wherein the porous substrate is made of paper or electrolyte-infused paper so as to form a transfer path through which ions may flow, and the anode and cathode are formed by materials printed on the paper.

20. The method of claim 12, wherein the output transducer includes an antenna connected to amplify the output signal, and the output transducer and antenna are 3D printed or screen printed onto the porous substrate.

21. The method of claim 12, wherein the output transducer includes a capacitor to store up and discharge power to an antenna.

22. The method of claim 12, wherein there are a plurality of anode and cathode pairs on the substrate connected in series or parallel.

* * * * *